United States Patent [19]
Dominguez et al.

[11] Patent Number: 5,639,739
[45] Date of Patent: Jun. 17, 1997

[54] IMIDAZOLE CONTAINING AMINOBORONIC ACIDS

[75] Inventors: Celia Dominguez; Joseph Cacciola, both of Newark, Del.; John Matthew Fevig, New London, Pa.

[73] Assignee: The DuPont Merck Pharmaceutical Company, Wilmington, Del.

[21] Appl. No.: 409,573

[22] Filed: Mar. 24, 1995

[51] Int. Cl.$^6$ .............. A61K 31/69; C07F 5/02; C07F 5/04; C07K 5/065

[52] U.S. Cl. .............. 514/64; 514/18; 514/19; 530/331; 544/60; 544/69; 544/229; 546/13; 548/110

[58] Field of Search ............... 548/110; 544/60, 544/69, 229; 546/13; 514/64, 18, 19; 530/331

[56] References Cited

U.S. PATENT DOCUMENTS

| | | | |
|---|---|---|---|
| 4,499,082 | 2/1985 | Shenvi et al. | 514/2 |
| 4,537,773 | 8/1985 | Shenvi | 514/63 |
| 5,106,948 | 4/1992 | Kinder et al. | 530/331 |
| 5,169,841 | 12/1992 | Kleeman et al. | 514/63 |
| 5,187,157 | 2/1993 | Kettner et al. | 530/331 |
| 5,288,707 | 2/1994 | Metternich | 530/331 |
| 5,332,822 | 7/1994 | Misra | 546/164 |
| 5,444,049 | 8/1995 | de Nanteuil et al. | 562/445 |
| 5,462,964 | 10/1995 | Fevig et al. | 514/213 |
| 5,543,526 | 8/1996 | Mallart et al. | 558/288 |

FOREIGN PATENT DOCUMENTS 677531  10/1995  European Pat. Off. .

OTHER PUBLICATIONS

Kettner et al, *Journal of Biological Chemistry,* 265, pp. 18289–18297 (190).

*Primary Examiner*—Emily Bernhardt

[57] ABSTRACT

The present invention relates generally to α-aminoboronic acids and corresponding peptide analogs of the formula (I):

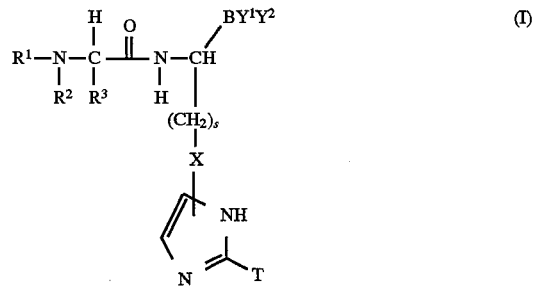

in which the α-carbon is substituted with an optionally functionalized imidazole containing alkyl group. These compounds are useful as inhibitors of trypsin-like serine protease enzymes, especially thrombin, Factor X and Factor VII.

3 Claims, No Drawings

IMIDAZOLE CONTAINING AMINOBORONIC ACIDS

FIELD OF THE INVENTION

The present invention relates generally to α-aminoboronic acids and corresponding peptide analogs in which the α-carbon is substituted with an optionally functionalized imidazole containing alkyl group. These compounds are useful as inhibitors of trypsin-like serine protease enzymes, especially thrombin, Factor X and Factor VII.

BACKGROUND OF THE INVENTION

Simple boronic acids are inhibitors of serine proteases. For example, Koehler et al. *Biochemistry* 10: 2477 (1971) reports that 2-phenylethane boronic acid inhibits chymotrypsin at millimolar levels. The synthesis of boronic acid analogs of N-acyl-α-amino acids has yielded more effective inhibitors. Acborophe-OH, R-1-acetamido-2-phenylethane boronic acid, inhibits chymotrypsin with a $K_i$ of 4 μM Matteson et al. *J. Am. Chem. Soc.* 103: 5241 (1981). More recently, Shenvi, U.S. Pat. No. 537,773 (1985) disclosed that boronic acid analogs of α-amino acids, containing a free amino group, were effective inhibitors of aminopeptidases. Shenvi, U.S. Pat. No. 4,499,082 (1985) discloses that peptides containing an α-aminoboronic acid with a neutral side chain were more effective inhibitors of serine proteases exceeding inhibitors disclosed earlier by as much as 3 orders of magnitude in potency. The chemistry of α-aminoboronic acids was further expanded to the synthesis of peptide analogs containing boronic acid with positive charged sidechains, boroLysine, boroArginine, boroOrnithine, and isothiouronium analogs (EPA 0 293 881, Dec. 7, 1988). This series of compounds have provided highly effective inhibitors of thrombin and other trypsin-like enzymes. The boroArginine analogs specifically designed as thrombin inhibitors are highly effective in the inhibition of blood coagulation both in vitro and in vivo.

It should be noted that additional boronic acids have been disclosed. Metternich (EP 0471651) have described peptides containing boroArginine and boroLysine which contain at least one unnatural amino acid residue. Elgendy et al. *Tetrahedron Lett.*, 33, 4209–4212 (1992) have described peptides containing α-aminoboronic acids with aliphatic neutral sidechains which are thrombin inhibitors. Kakkar in (WO 92/07869) has claimed peptide thrombin inhibitors of the general structure, X—Aa$_1$—Aa$_2$—NH—CH(Y)—Z where Aa$_1$ and Aa$_2$ are unnatural amino acid residues. Z is —CN, —COR, —B(R$^2$)(R$^3$), —P(O)(R)(R), and Y is —[CH$_2$]$_n$—Q or —CH$_2$—Ar—Q where Q=H, amino, amidino, imidazole, guanidino or isothioureido and n=1–5 and where R$_2$ and R$_3$ are the same or different and are selected from the group consisting of OH, OR$^6$, and NR$^6$R$^7$, or R$^2$ and R$^3$ taken together represent the residue of a diol.

Electrophilic tripeptide analogs containing the ((D-phenylalanyl)prolyl)—arginyl—sequence are well known as effective inhibitors of the trypsin-like serine protease thrombin. H-(D) Phe-Pro-ArgCH$_2$Cl was first reported by Kettner and Shaw (*Thromb. Res.* 14, 969 (1979)) to be a selective but irreversible inhibitor of human thrombin. A number of studies looking for alternatives to the electrophilic P$_1$ argininechloromethylketones that would yield a reversible protease inhibitor have been reported. Bajuez et al. (*Folia Haematol.* 109, s. 16 (1982)) found the corresponding aidehyde, D-phenylalanyl-prolyl-arginal, to be a reversible thrombin inhibitor with a $K_i$=75 nM for human thrombin. The nitrile analog, D-phenylalanyl-prolyl-NHCH((CH$_2$)$_3$NHC(=NH)NH$_2$)—CN, was found to be substantially less potent with a $K_i$=700 nM (Kaiser et al., *Pharmazie* 46, 128 (1991)). A retroamide inhibitor, with the D-phenylalanyl-prolyl-sequence and 2-(4-guanidinophenylalanyl)-N-acetyl-2,2-difluoroethylamine substituting for an electrophilic arginine derivative, is a good inhibitor with a $K_i$ of 70 nM for thrombin (Altenburger and Schirlin, *Tetrahedron Lett.* 32, 7255 (1991)). Cheng et al. claim that the substitution of racemic diphenyl 1-amino-4-methoxybutylphosphonate for an electrophilic arginine derivative gives very good inhibitors with a $K_i$=4.8 nM (*Tetrahedron Lett.* 32, 7333 (1991)). Iwanowicz et al. (*Bioorgan. Med. Chem. Lett.* 2, 1607 (1992)) has studied the efficacy of (D-phenylalanine)prolyl-conjugated to —NHCH[(CH$_2$)$_4$NH$_2$]CH(OH)CO$_2$Me) and —NHCH[(CH$_2$)$_4$NH$_2$]C(=O)CO$_2$Me derivatives. The most effective inhibitor of human thrombin reported to date is the boropeptide acetyl-D-phenylalanyl-prolyl-boro arginine with a $K_i$=0.041 nM (Kettner et al., *J. Biol. Chem.* 265, 18289 (1990)).

Walker et al. (*Biochem. J.* 230, 645 (1985)) published a comparative study of irreversible thrombin inhibitors based on the D-phenylalanyl-prolyl-argininyl sequence confirming the earlier report by Kettner and Shaw (1979). H-(D) Phe-Pro-ArgCH$_2$Cl was found to be the most effective inhibitor ($K_i$=25 nM) while replacing the D-phenylalanine with 4-amino-D-phenylalanine or ω-benzoyl-D-lysine gave less active analogs. Compounds in development include -(prolyl) arginal derivatives with a variety of unusual P$_3$ amino acids including D-N-methylphenylglycine, Boc-D-fluorophenylglycine as well as constrained cyclized derivatives of D-phenylglycine and D-phenylalanine (Shuman et. al., *J. Med. Chem.* 36, 314 (1993)). Balasubramanian et al. (*J. Med. Chem.* 36, 300 (1993)) has reported an extensive study of replacements for the P$_3$ D-phenylalanine of D-phenylalanyl-prolyt-arginal and found the dihydrocinnamoyl group to be effective, although somewhat less potent.

Patent disclosures in this area have centered around suitably protected peptides composed of natural and unnatural amino acids. In U.S. Pat. No. 5,187,157 DuPont Merck has disclosed peptides comprised of C-terminal boronic acid derivatives of lysine, ornithine and arginine as reversible inhibitors of trypsin-like serine proteases. In European Patent Application EP 471 651 A2 Sandoz disclosed borolysine and boroarginine peptide analogs containing at least one unnatural hydrophobic α-amino acid substituted with groups such as the trimethylsilyl- or naphthyl-. In U.S. Pat. No. 5,106,948 was disclosed a series of boropeptides that are effective as cytotoxic agents. In PCT Application WO 92/07869, Thrombosis Research Institute has disclosed tripeptide analogs containing a P$_2$ proline and an unnatural disubstituted amino acid at P$_3$. A variety of electrophilic and non-electrophilic α-amino acid analogs were claimed as suitable P$_1$ substituents. Tripeptide antithrombotic agents limited to α-alkyl and α-aryl or heteroaryl substituted glycines at P$_3$ conjugated to -(prolyl)arginal were disclosed by Lilly (European Patent Application EP 479 489 A2). Marion Merrell Dow disclosed a series of activated electrophilic ketone analogs of peptidase substrates useful for inhibiting serine-, carboxylic acid- and metallo- proteolytic enzymes; compounds are peptides composed of suitably protected α-amino acids conjugated to an electrophilic ketone derivative of an α-amino acid (European Patent Applications EP 417 721 A2, EP 364 344 A2, EP 363 284 A2, EP 195 212 A2). Astra has disclosed a series of α-((trifluoroethyl) oxymethyl)-arginine tripeptides (European Patent Application EP 0 530 167 A). Georgia Tech Research Corporation disclosed peptidyl ketoamides, -ketoacids and -ketoesters as inhibitors of serine and cysteine proteases (WO 92/12140). Boehringer Ingelheim disclosed a series of trifluoromethyl- and α,α-difluoromethyl-β-ketoesterpeptide derivatives as elastase inhibitors (EP 0 369 391 A2).

A number of naturally occurring thrombin inhibitors have been reported. These include nazumamide A from Theonella sp. (see Fusetani, et. al., *Tetrahedron Lett.* 1991, 32, 7073-4), cyclotheonamide A from Theonelia sp. (see Fusetani, et. al., *J. Am. Chem. Soc.* 1990, 112, 7053-4 (1990)), amblyommin from *Amblyomma hebraeum* (see Bonin, et. al., EP 345614), hirudin from *Hirudo medicinalis*, recombinant versions of hirudin and hirudin fragments (see Rigbi and Jackson, EP 352903, Koerwer, WO 9109946, Meyer, et. al., WO 9108233, Dawson, et. al., WO 9109125, Maraganore, et. al., WO 9102750 and Maraganore, EP 333356).

Synthetic thrombin inhibitors have also been disclosed. Arylsulfonylarginine amides such as (2R,2R)-4-methyl-1-[$N^2$-{(3-methyl-1,2,3,4-tetrahydro-8-quinolinyl) sulfonyl}-L-arginyl]-2-piperidinecarboxylate have been shown to be effective inhibitors of thrombin (see Okamoto, et. al. *Thromb Res.*, 8, 77–82 (1976), Ohshiro, et. al., *Blood Vessel*, 14, 216-8 (1983)), as have compounds containing constrained arginine mimics such as (2-naphthylsulfonylglycyl) -4-amidino-phenylalanyl piperidide (see Stuerzebecher, et. al., *Thromb. Res.*, 29, 635–42 (1983)), 1-[2-[5-(dimethylamino)naphth-1-ylsulfonamido]-3-(2-iminohexahydropyrimidin-5-yl)propanoyl]-4-methylpiperidine dihydrochloride (see Ishikawa, JP 88227572 and Ishikawa and Inamura, JP 88227573), N-(trans-4-amino-methylcyclohexylcarbonyl)-4-O-(2-picolyl)-L-tyrosine 4-acetanilide dihydrochloride (see Okamoto, et. al., EP 217286) and 4-[(aminoiminomethyl) amino]benzoic acid esters (see Fuji, et. al., DE 3005580, Matsuoka, et. al., *Jpn. J. Pharmacol.*, 51, 455–63 (1989), and Takeshita, et. al., EP 435235).

Inhibitor design has benefitted from the knowledge of the mechanism of action and of the peptide sequences which are thought to bind in the catalytic site of thrombin, e.g., -Gly-Vat-Arg-Gly- of fibrinogen (see Blomback, et. al., *J. Biol. Chem.*, 247, 1496–512 (1972)), Ile-Pro-Arg-Ser- of prothrombin (see Magnussen, et. al., in: Reich, et. al., "Proteases and Biological Control," pp. 123–149 (1975)) and -Val-Pro-Arg-Gly- of factor XIII (see Takagi and Doolittle, *Biochemistry*, 13, 750–6 (1974), and Nakamura, et. al., *Biochem. Biophys. Res. Commun.*, 58, 250–256 (1974)). This class of mechanism-based inhibitors are exemplified by the tripeptide aldehyde D-Phe-Pro-N-Me-Arg-H (see Bajuez, et. al., *J. Med. Chem.*, 33, 1729–35 (1990)), and the trifluoromethyl ketone D-Phe-Pro-ArgCF$_3$ (see Kolb, et. al., U.S. Pat. No. 697987).

Surprising for their lack of a basic residue at P$_1$ are tripeptide thrombin inhibitors comprised of 1-aminoboronic and 1-aminophosphonic acid analogs of 3-methoxy-propylglycine (see Claeson, et. al., U.S. 07-245,428) and pentylglycine (see Cheng, et. al., "Symposium on Thrombosis and Hemostasis,"1991, Amsterdam, Abstract 2150).

In addition to thrombin inhibition, boropeptides have been disclosed with utility as a treatment for tumors, viral infections and arthritis (US 4963655A and EP 354522A), hypertension (EP 315574A) and as factor VII/VIIa inhibitors (WO 8909612A). Kleemann, et. al. (AU A-24693/88) disclose renin-inhibiting 1-amino boronic acid derivatives of formula (3)

   (3)

in which A$^1$ denotes a radical of formulae (4–8).

   (4)

   (5)

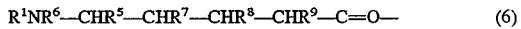   (6)

   (7)

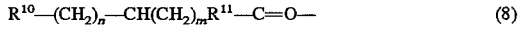   (8)

A recently issued Patent (U.S. Pat. No. 5,332,822, issued Jul. 26, 1994, R. N. Misra) claims compounds of the general formula (9) which are useful as thrombin inhibitors. Substituent definitions are as follows: R$^1$ and R$^2$ are independently H, lower alkyl, cycloalkyl, aryl, heteroaryl, or heteroarylalkyl; or together R$^1$ and R$^2$ are a heterocycle containing N, S, and/or O optionally substituted with lower alkyl, carboxy, amido, carboalkoxy, aryl, cycloalkyl, hydroxy, amino, alkylamino, or dialkylamino. R$^3$ is heteroaryl. R$^4$ is alkyl, cycloalkyl, aryl, tetrahydronaphthyl, heteroaryl, quinolinyl, or tetrahydroquinolinyl. No biological data is disclosed.

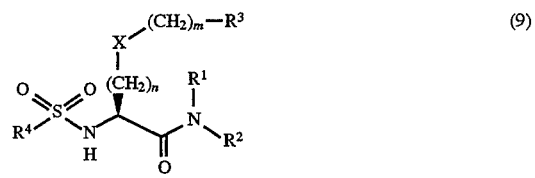   (9)

Despite the foregoing, more efficacious and specific inhibitors of coagulation proteases are needed as potentially valuable therapeutic agents for the treatment of thrombosis. None of the cited references describe or suggest the new thrombin-inhibiting boronic acid derivatives of the present invention.

The present invention concerns dipeptides which contain an electrophilic derivative of an α-amino acid at P$_1$ (where P$_1$ is the carboxyl terminus of the dipeptide). The P$_1$ substituent contains an optionally functionalized imidazole group, and the P1 is conjugated to an N,N-disubstituted or N-monosubstituted α-amino acid at P$_2$ (where P$_2$ is the end-terminus of the dipeptide). The electrophilic functional groups used to derivatize the P$_1$ amino acid analog are boronic acids and their esters. The N,N-disubstituted α-amino acids are derivatives of an amino acid other than proline where the α-amino group is alkylated and acylated or diacylated to give alicyclic or cyclic substituents.

SUMMARY OF THE INVENTION

[1] The present invention provides novel compounds of formula (I):

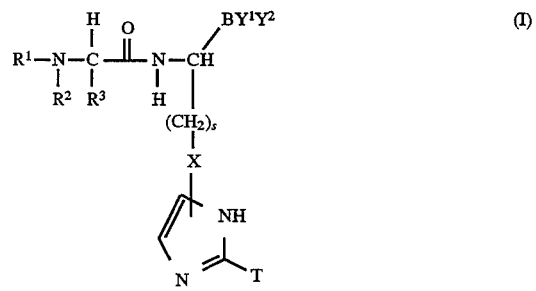   (I)

or a pharmaceutically acceptable salt, hydrate or prodrug thereof, wherein:

R$^1$ is a) —C(=O)—CH[(CH$_2$)$_r$R$^4$]—NR$^5$R$^6$
b) —C(=O)—CR$^8$R$^9$—(CH$_2$)$_p$—R$^4$,
c) —C(=O)—CR$^8$R$^9$—W—(CH$_2$)$_r$—R$^4$,
d)

[structure: C(=O)-phenyl-(CH$_2$)$_r$-Ph]

e)

[structure: C(=O)-phenyl-W-(CH$_2$)$_r$-Ph]

f)

[structure: C(=O)-CH(aryl)-CH-(CH$_2$)$_n$ ring]

g)

[structure: C(=O)-CH(aryl)-CH-W ring]

R$^2$ is
a) —CH$_2$C(R$^{12}$)$_2$-arly,
b) —CH$_2$C(R$^{12}$)$_2$-heteroaryl, or
c)

[cyclopropyl structure with aryl or heteroaryl and CH$_2$]

R$^3$ is
a) hydrogen, or
b) R$^2$ and R$^3$ can be taken together to form:

[pyrrolidinone structure with R$^1$—N]

R$^4$ is
a) hydrogen,
b) C$_1$-C$_4$ alkyl,
c) aryl,
d) heteroaryl, or
e) C$_3$-C$_8$ cycloalkyl;

R$^5$ is
a) hydrogen,
b) C$_1$-C$_4$ alkyl, or
c) —(C$_1$-C$_4$ alkyl)-aryl;

R$^6$ is
a) —C(=O)—R$^7$,
b) —C(=O)—OR$^7$,
c) —C(=O)—NR$^5$R$^7$,
d) —S(O)$_2$—R$^7$, or
e) —S(O)$_2$—NR$^5$R$^7$;

R$^7$ is
a) C$_1$-C$_4$ alkyl, or
b) —(C$_1$-C$_4$ alkyl)-aryl;

R$^8$ and R$^9$ are independently:
a) hydrogen,
b) C$_1$-C$_4$ alkyl,
d) aryl, or
e) —(C$_1$-C$_4$ alkyl)-aryl;

R$^8$ and R$^9$ can be taken together to form a (C$_3$-C$_7$) cycloalkyl;

R$^{10}$ and R$^{11}$ are independently:
a) hydrogen,
b) C$_1$-C$_4$ alkyl,
c) —(C$_1$-C$_4$ alkyl)-aryl,
d) (C$_5$-C$_7$) cycloalkyl, or
e) aryl;

R$^{10}$ and R$^{11}$ can be taken together to form:

[—N ring with W, or —N ring with (CH$_2$)$_n$]

R$^{12}$ is
a) —(C$_1$-C$_5$) alkyl, or
b) —(C$_1$-C$_5$) fluoroalkyl;

aryl is phenyl or phenyl optionally substituted with from one to three groups selected independently from:

F, Cl, Br, I, C$_1$-C$_4$ alkyl, C$_1$-C$_4$ alkoxy, methylenedioxy, —NO$_2$, —CF$_3$, —S(O)$_r$—(C$_1$-C$_4$ alkyl), CN, OH, —NH$_2$, —NH(C$_1$-C$_4$ alkyl), —N(C$_1$-C$_4$ alkyl)$_2$, —NHC(=O) (C$_1$-C$_4$ alkyl), —(CH$_2$)$_p$—CO$_2$ (C$_1$-C$_4$ alkyl), or phenyl;

heteroaryl is
2-, 3-, or 4-pyridinyl, 2- or 3-thienyl, 2-, 4-, or 5-pyrimidinyl, 2-, 4-, or 5-oxazolyl, or 2-, 4-, or 5-thiazolyl, optionally substituted with from one to three groups selected independently from: F, Cl, Br, I, C$_1$-C$_4$ alkyl, C$_1$-C$_4$ alkoxy, methylenedioxy, —NO$_2$, —CF$_3$, —S(O)$_r$—(C$_1$-C$_4$ alkyl), CN, —OH, —NH$_2$, —NH(C$_1$-C$_4$ alkyl), —N(C$_1$-C$_4$ alkyl)$_2$, —NHC(=O) (C$_1$-C$_4$ alkyl), —(CH$_2$)$_p$—CO$_2$ (C$_1$-C$_4$ alkyl), or phenyl;

T is
a) H
b) —NH$_2$, or
c) —NO$_2$;

W is
a) —O—,
b) —S(O)$_r$—,
c) —NR$^5$—, or
d) —NC(=O) R$^7$—;

X is
a) S,
b) O,
c) CH$_2$,
d) NH, or
e) a single bond;
provided that when X is bound to a nitrogen, then X is not a heteroatom;

Y$^1$ and Y$^2$ are a) OR$^5$,
b) —F,
c) —NR$^{10}$R$^{11}$, or when taken together Y$^1$ and Y$^2$ form:

d) a cyclic boron ester where said chain or ring contains from 2 to 20 carbon atoms and, optionally, 1–3 heteroatoms which can be N, S, or O,
e) a cyclic boron amide where said chain or ring contains from 2 to 20 carbon atoms and, optionally, 1–3 heteroatoms which can be N, S, or O,
f) a cyclic boron amide-ester where said chain or ring contains from 2 to 20 carbon atoms and, optionally, 1–3 heteroatoms which can be N, S, or O;

n is 0 or 1;
p is 0 to 3;
r is 0 to 2;
s is 1 to 4; and
t is 1 to 3.

Preferred is a compound of the formula (IA)

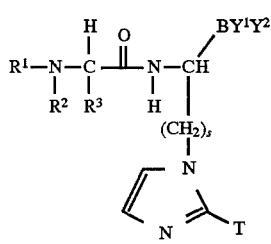

or a pharmaceutically acceptable salt, hydrate, or prodrug thereof, wherein:

R$^1$ is
a) —C(=O)—CH[(CH$_2$)$_n$R$^4$]—NR$^5$R$^6$
b) —C(=O)—CR$^8$R$^9$—(CH$_2$)$_p$—R$^4$, or
c) —C(=O)—CR$^8$R$^9$—W—(CH$_2$)$_r$—R$^4$;

R$^2$ is
a) —CH$_2$C(R$^{12}$)$_2$-aryl,
b) —CH$_2$C(R$^{12}$)$_2$-heteroaryl, or
c)

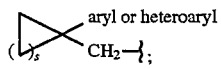

R$^3$ is
a) hydrogen, or
b) R$^2$ and R$^3$ can be taken together to form:

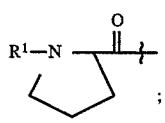

R$^4$ is
a) aryl,
b) heteroaryl, or
c) C$_3$–C$_8$ cycloalkyl;

R$^5$ is
a) hydrogen, or
b) —(C$_1$14 C$_4$ alkyl)-aryl;

R$^6$ is
a) —C(=O)—R$^7$,
b) —C(=O)—OR$^7$,
c) —C(=O)—NR$^8$R$^7$,
d) —S(O)$_2$—R$^7$, or
e) —S(O)$_2$—NR$_5$R$^7$;

R$^7$ is
a) C$_1$–C$_4$ alkyl, or
b) —(C$_1$–C$_4$ alkyl)-aryl;

R$^8$ and R$^9$ are independently:
a) hydrogen,
b) C$_1$–C$_4$ alkyl,
d) aryl, or
e) —(C$_1$–C$_4$ alkyl)-aryl;

R$^8$ and R$^9$ can be taken together to form a (C$_3$–C$_7$) cycloalkyl;

R$^{12}$ is
a) —(C$_1$–C$_5$) alkyl, or
b) —(C$_1$–C$_5$) fluoroalkyl;

aryl is phenyl or phenyl optionally substituted with from one to three groups selected independently from:
F, Cl, Br, I, C$_1$–C$_4$ alkyl, C$_1$–C$_4$ alkoxy, methylenedioxy, —NO$_2$, —CF$_3$, —S(O)$_r$—(C$_1$–C$_4$ alkyl), CN, —OH, —NH$_2$, —NH(C$_1$–C$_4$ alkyl), —N(C$_1$–C$_4$ alkyl)$_2$, —NHC(=O) (C$_1$–C$_4$ alkyl), —(CH$_2$)$_p$—CO$_2$ (C$_1$–C$_4$ alkyl), or phenyl;

heteroaryl is
2-, 3-, or 4-pyridinyl, 2- or 3-thienyl, 2-, 4-, or 5-pyrimidinyl, 2-, 4-, or 5-oxazolyl, or 2-, 4-, or 5-thiazolyl, optionally substituted with from one to three groups selected independently from: F, Cl, Br, I, C$_1$–C$_4$ alkyl, C$_1$–C$_4$ alkoxy, methylenedioxy, —NO$_2$, —CF$_3$, —S(O)$_r$—(C$_1$–C$_4$ alkyl), CN, —OH, —NH$_2$, —NH(C$_1$–C$_4$ alkyl), —N(C$_1$–C$_4$ alkyl)$_2$, —NHC(=O) (C$_1$–C$_4$ alkyl), —(CH$_2$)$_p$—CO$_2$ (C$_1$–C$_4$ alkyl), or phenyl;

T is —NH$_2$; and

Y$^1$ and Y$^2$ are
a) —OH, or
when taken together Y$^1$ and Y$^2$ form:
b) a cyclic boron ester where said chain or ring contains from 2 to 20 carbon atoms and, optionally, 1–3 heteroatoms which can be N, S, or O;

n is 0 or 1;
p is 0 to 3;
r is 0 to 2;
s is 1 to 4; and
t is 1 to 3.

This invention also provides compositions comprising one or more of the foregoing compounds and methods of using such compositions in the treatment of aberrant proteolysis such as thrombosis in mammals or as reagents used as anticoagulants in the processing of blood to plasma for diagnostic and other commercial purposes.

DETAILED DESCRIPTION OF THE INVENTION

As used throughout the specifications, the following abbreviations for amino acid residues or amino acids apply:

Ala=L-alanine
Arg=L-arginine
Ash=L-asparagine
Asp=L-aspartic acid
Aze=azedine-2-carboxlic acid
Cys=L-cysteine
Gln=L-glutamine
Glu=L-glutamic acid
Gly=glycine His=L-histidine
HomoLys=L-homolysine
Ile=L-isoleucine
Irg=isothiouronium analog of L-Arg
Leu=L-leucine
Lys=L-lysine
Met=L-methionine
Orn=L-ornithine
Phe=L-phenylalanine
Pro=L-proline
Ser=L-serine
Thr=L-threonine
Trp=L-tryptophan
Tyr=L-tyrosine
Val=L-valine
Sar=L-sarcosine
Phe(4-fluoro)=para-fluorophenylalanine The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic acid ester. For example, if $Y^1$ and $Y^2$ are OH, the C-terminal residue is abbreviated "boroGly-OH" where "—OH" indicates the boronic acid is in the form of the free acid. The pinanediol boronic acid ester and the pinacol boronic acid ester are abbreviated "—$C_{10}H_{16}$" and "—$C_6H_{12}$", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Compound containing functional groups on Analogs containing sidechain substituents are described by indicating the substituent in parenthesis and/or brackets following the name of the parent residue. For example, the compound where, $Y^1$ and $Y^2$ are —OH, and $H^2$ is a 2-aminoimidazol-1-yl group is abbreviated boroGly [$(CH_2)_3$-(2-aminoimidazol-1-yl)]—OH. Other abbreviations are: Cbz, benzyloxycarbonyl; BSA, benzene sulfonic acid; THF, tetrahydrofuran; Boc-, t-butoxycarbonyl-; Ac-, acetyl; pNA, p-nitro-aniline; DMAP, 4-N,N-dimethylaminopyridine; Tris, Tris(hydroxymethyl) aminomethane; MS, mass spectrometry; FAB/MS, fast atom bombardment mass spectrometry. LRMS($NH_3$—CI) and HRMS($NH_3$—CI) are low and high resolution mass spectrometry, respectively, using $NH_3$ as an ion source.

The following abbreviations are used herein and are defined as follows. The abbreviation "DIBAl" means diisobutylaluminum hydride. The abbreviation "RaN" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "DMF" means dimethyl formamide. The abbreviation "EtOH" means ethanol.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

When any variable (for example, $R^{11}$, $R^{12}$, $R^{13}$, m, etc.) occurs more than one time in any substituent or formula for a compound, its definition on each occurrence is independent of its definition at every other occurrence. Thus, for example, if a group is shown to be substituted with 0–3 $R^{11}$, then said group may optionally be substituted with up to three $R^{11}$ meanings and $R^{11}$ at each occurrence is selected independently from the defined list of possible $R^{11}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —$C(R^{11})_2$—, each of the two $R^{11}$ substituents on C is independently selected from the defined list of possible $R^{11}$.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperidinyl, unless specified otherwise, said piperidinyl group may be bonded to the rest of the compound of a given formula via any atom in said piperidinyl group.

As used herein, "alkyl" is intended to include both branched and straight-chain saturated aliphatic hydrocarbon groups having the specified number of carbon atoms; "fluoroalkyl" is intended to include both branched and straight-chain saturated aliphatic hydrocarbon groups having the specified number of carbon atoms, substituted with 1 or more flurines (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono- or bicyclic ring systems, such as cyclopropyl, cyclobutyl, cyclopentyl, cyclohexyl and so forth.

The term "($C_1$–$C_4$ alkyl)aryl" is intended to refer to a $C_1$–$C_4$ alkyl group which is attached through an aryl ring to the residue of the indicated compound.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e.,=O), then 2 hydrogens on the atom are replaced.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the compounds of formula (I); phosphate esters, dimethylglycine esters, aminoalkylbenzyl esters, aminoalkyl esters and carboxyalkyl esters of alcohol and phenol functional groups in the compounds of formula (I); and the like.

The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Synthesis

The compounds of the invention of formula —$(CH_2)_s$—NH—$H^1$ ($H^1$ is 2-(T)imidazol-4- or 5-yl) are made according to Scheme 1. Amine 1 is readily available via the procedure of Kettner and Shenvi (EP 0293881 A2, *J. Biol. Chem.* 265, 18289–18297, (1990). There are numerous synthetic methods by which to prepare amide 2; however, competing with amide formation is the cyclization of 1 to afford a complex mixture containing the desired amide and the corresponding N-acylboroproline. Three methods are preferred for the preparation of 2. In the first, solution of 1 in tetrahydrofuran or dichloromethane at 0° C. is treated sequentially with the desired acid chloride followed by two equivalents of triethylamine. The mixture is then allowed to warm up to room temperature overnight. The second method, is the mixed anhydride procedure of Anderson et. al. (*J. Am. Chem. Soc.*, 89 5012 (1967)). In this method the isobutyl mixed anhydride is generated by dissolving the carboxylic acid component in tetrahydrofuran and adding one equivalent of N-methylmorpholine (NMM). The solution is cooled to 0° C. and one equivalent of isobutyl chloroformate (IBCF) is added, followed by the addition of one equivalent of triethylamine. The mixture is typically stirred at 0° C. for one hour followed by several hours at room temperature. The third method for amide formation is the hydroxybenzotriazole/DCC method of König and Geiger (*Chem. Ber.*, 103, 788–98 (1970)). Thus, to a solution of I and the carboxylic acid component in dimethylformamide or tetrahydrofuran at 0° C. is added N-methylmorpholine, 1-hydroxybenzotriazole hydrate (2.0 eq) and DCC (1.05 eq). The solution is allowed to warm to room temperature overnight.

The preferred method for the preparation of azide 3 is by reaction of 2 with sodium azide (1.1 eq) in dimethylformamide at 70° C. for 2 hours. Reduction of azide 3 to amine 4 may be accomplished by hydrogenation over precious metal catalysts. The preferred catalyst for this transformation is Pearlman's catalyst (palladium hydroxide on carbon). The product is typically isolated as the hydrochloride salt. Salts of 4 which may confer superior physical properties may be preferred over the hydrochloride salt. Addition of amine 4 to $H^1$—L (L=Cl, Br) is accomplished in $Et_3N$ and DMF at 70° C. for 18 hours. This affords the hetercocyclic inhibitor 5. The conversion of 5 to 6 is accomplished via transesterification with phenyl boronic acid.

Scheme 1.

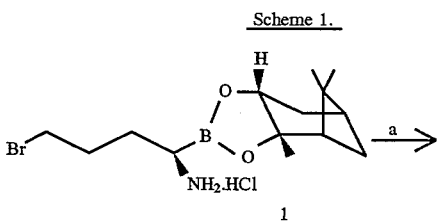

1

Scheme 1.
-continued

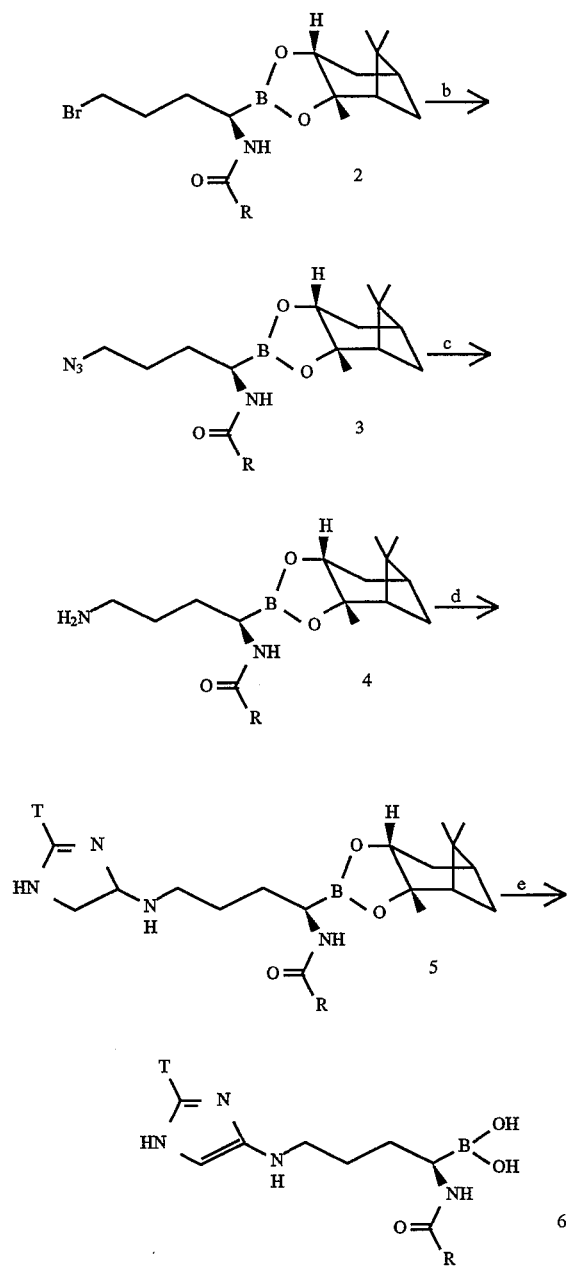

Reagents: a. IBCF, NMM, RCO$_2$H, Et$_3$N, 0° C.; b. NAN$_3$; c. H$_2$, Pd(OH)$_2$/C, HCl; d. Et$_3$N, DMF, H$^1$—L (L is a leaving group); e. phenylboronic acid.

The compounds of the invention of formula —(CH$_2$)$_2$—X—H$^1$ (H$^1$ is 2-(T) imidazol-4- or 5-yl) may also be prepared according to Scheme 2. Thus, refluxing 2 in DMF or EtOH in the presence of H$^1$—X—H and a base such as K$_2$CO$_3$ affords 7. The free boronic acid 8 may be obtained from 7 following the procedure in Scheme 1.

Scheme 2.

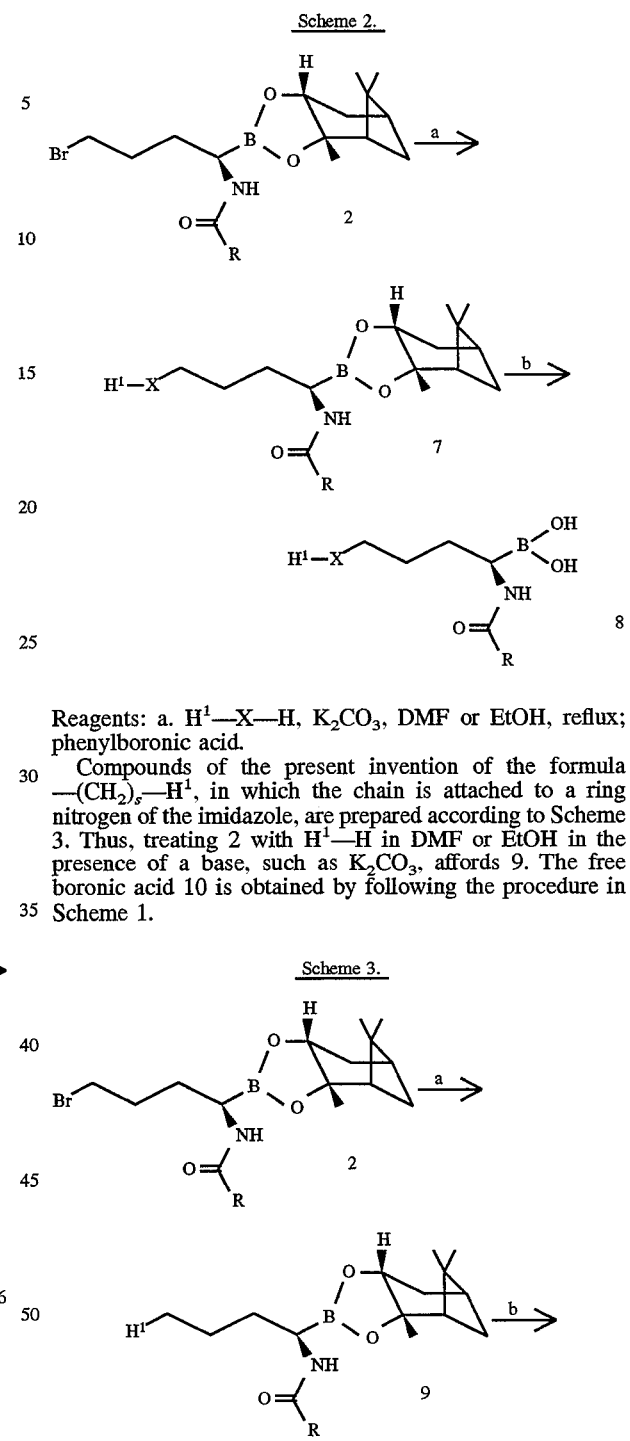

Reagents: a. H$^1$—X—H, K$_2$CO$_3$, DMF or EtOH, reflux; phenylboronic acid.

Compounds of the present invention of the formula —(CH$_2$)$_s$—H$^1$, in which the chain is attached to a ring nitrogen of the imidazole, are prepared according to Scheme 3. Thus, treating 2 with H$^1$—H in DMF or EtOH in the presence of a base, such as K$_2$CO$_3$, affords 9. The free boronic acid 10 is obtained by following the procedure in Scheme 1.

Scheme 3.

Reagents: a. H$^1$—H, K$_2$CO$_3$ (base), DMF or EtOH; b. phenyl boronic acid

Compounds of the present invention of the formula —(CH$_2$)$_{1-4}$H$^1$, in which the chain is attached to a ring carbon of the imidazole, are prepared as shown in Schemes 4–6. Scheme 4 is an extension of the chemistry of Kettner and Shenvi (EP 0293881 A2, *J. Biol. Chem.* 265, 18289–18297, 1990) wherein the olefins 17 are employed. The imidazole is properly functionalized and protected for the reaction conditions (M. P. Groziak *J. Org. Chem.* 1192 57,33776 and B. H. Lipshutz Tet. Lett. 1992 33 (40), 5865).

Scheme 4.

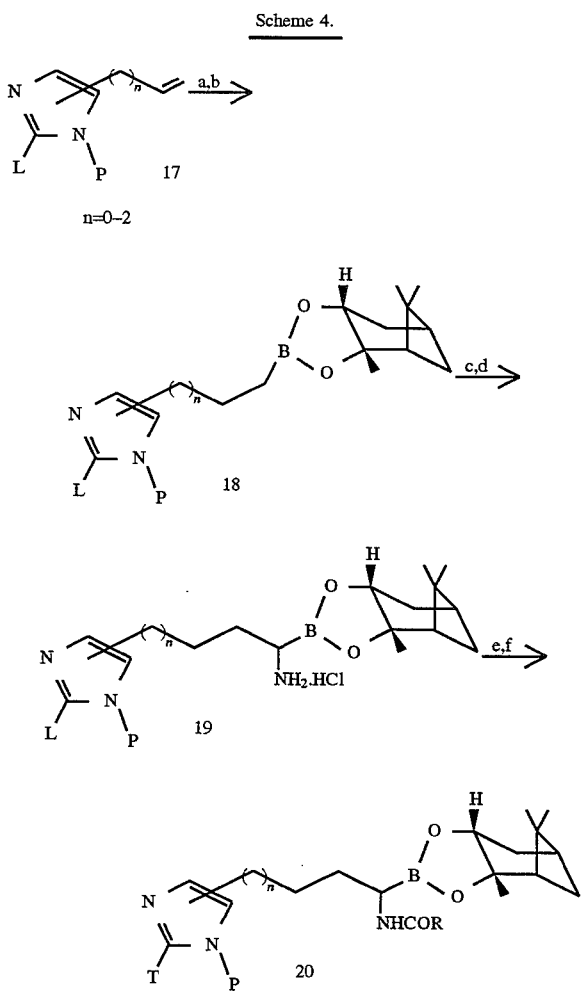

Reagents: a. catechol borane (L is a leaving group or and P is a protecting group); b. pinanediol; c. LiCHCl$_2$, then ZnCl$_2$; d. LiN(TMS)$_2$, then HCl; e. RCOOH, NMM, IBCF, f. deprotection of L or proper functionalization.

Compounds of the present invention of formula —(CH$_2$)$_s$—H$^1$ (H$^1$ is imidazol-4- or 5-yl) may be obtained via a metal coupling reaction with dichloropinanediolboronate [*Organometalics* 2, 1543–1545 (1983)], M-heterocycle 26 were M=Mg, Zn or Li, and CuCN.LiCl [Berk et al. Organometallics 9, 3053–3064 (1990)]. (Scheme 5) The desired product 28 is achieved via the procedure as for amide 2 in Scheme 1. Followed by appropriate manipulation of the protecting groups (M. P. Groziak J. Org. Chem. 1192 57.33776 and B. H. Lipshutz Tet. Lett. 1992 33 (40), 5865 ).

Scheme 5.

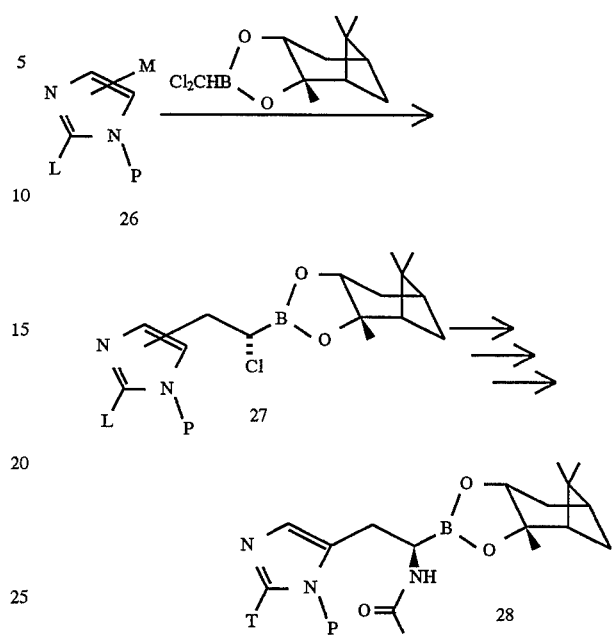

EXAMPLE 1

Synthesis of Acetyl-(D)-Phe-Pro-boroGly-[(CH$_2$)$_3$-(2-aminoimidazo-1-yl)]-C$_{10}$H$_{16}$ Acetyl-(D)-phe-pro-boroGly-[(CH$_2$)$_3$-NH$_2$. HCl (prepared according to EP0293881; 500 mg, 0.81 mmol), 2-nitroimidazole (81mg, 0.81mmol), and triethylamine (164 mg, 1.62 mmol) in DMF were heated at 80° C. for 18 h. The mixture was concentrated in vacuo, dissolved in ethyl acetate and washed with water, 0.1N HCl, brine, dried with Na$_2$SO$_4$, filtered and concentrated in vacuo to afford Acetyl-(D)-Phe-Pro-boroGly-[(CH$_2$)$_3$-(2-nitroimidazo-1-yl)]-C$_{10}$H$_{16}$ in 78% yield(411 mg, 0.63 mmol). FAB HRMS for C$_{33}$H$_{46}$BN$_6$O$_7$ calc.649.352104, found 649.353177.

Acetyl-(D)-Phe-Pro-boroGly-[(CH$_2$)$_3$-(2-nitroimidazo-1-yl)]-C$_{10}$H$_{16}$ (371 mg, 0.57 mmol) was reduced under catalytic conditions of Pd(OH)$_2$ (16 mg, 0.11 mmol) in ethanol under H$_2$ at r.t. for 5 h. The mixture was filtered through celite®, rinsed with ethanol and concentrated in vacuo to afford product in 60% yield (210 mg, 0.34 mmol).ESI LRMS (M+H)$^+$619.

The examples shown in Table 1, can be prepared by the schemes and procedures above using the appropriate starting materials. These examples are only meant to be illustrative of and are not to be construed as limiting the scope of the present invention.

TABLE 1

| EX | | LRMS Method | Calc | Found |
|---|---|---|---|---|
| 1 | Ac-(D)Phe-ProboroGly-[(CH$_2$)$_3$—NH-(2-nitro)-imidazol-1-yl]-C$_{10}$H$_{16}$ | ESI (M + H) | 649 | 649 |
| 2 | Ac-(D)Phe-ProboroGly-[(CH$_2$)$_3$—NH- | ESI (M + H) | 619 | 619 |

TABLE 1-continued

| EX | | LRMS Method | Calc | Found |
|----|---|---|---|---|
| | (2-amino)-imidazol-1-yl]-$C_{10}H_{16}$ | | | |
| 3 | Butanesulfonyl(D)Phe-ProboroGly-[(CH$_2$)$_3$—NH-(2-nitro)-imidazol-1-yl)]-$C_{10}H_{16}$ | ESI (M + H) | 727 | 727 |
| 4 | Butanesulfonyl(D)Phe-ProboroGly-[(CH$_2$)$_3$—NH-(2-amino)-imidazol-1-yl)]-$C_{10}H_{16}$ | ESI (M + H) | 697 | 697 |
| 5 | Ac-(D)Phe-ProboroGly-[(CH$_2$)$_3$-1-(imidazolyl)]-$C_{10}H_{16}$ | ESI (M + H) = | 604 | 604 |

Further illustrative of the scope of the present invention are the following compounds in Table 2 which may also be prepared according to the procedures and schemes above.

TABLE 2

| 6 | Hydrocinnamoyl-N-[2-cyclopropylphenethyl]GlyboroGly-[(CH$_2$)$_3$-(2-amino)imidazol-1-yl]-OH |
|---|---|
| 7 | Hydrocinnamoyl-N-[2-cyclopentylphenethyl]GlyboroGly-[(CH$_2$)$_3$-(2-amino)imidazol-1-yl]-OH |
| 8 | Hydrocinn-N-[2,2-dimethylphenethyl]GlyboroGly[(CH$_2$)$_3$-(2-amino)imidazol-1-yl]-OH |
| 9 | Hydrocinnamoyl-N-[2-cyclopropylphenethyl]GlyboroGly-[(CH$_2$)$_3$-(2-aminoimidazl-4-yl)-OH |
| 10 | Hydrocinnamoyl-N-[2-cyclopentylphenethyl]GlyboroGly-[(CH$_2$)$_3$-(2-amino)imidazol-4-yl]-OH |
| 11 | Hydrocinnamoyl-N-[2-cyclopentylphenethyl]GlyboroGly-[(CH$_2$)$_3$-(2-aminoimidazol-5-yl)-OH |
| 12 | Acetyl(D)Phe-ProboroGly-[(CH$_2$)$_3$—NH-(2-amino-imidazol-4-yl)]-OH |
| 13 | Acetyl(D)Phe-ProboroGly-[(CH$_2$)$_3$—NH-(2-amino-imidazol-5-yl)]-OH |
| 14 | Butanesulfonyl(D)Phe-ProboroGly-[(CH$_2$)$_3$—NH-(2-nitro-imidazol-4-yl)]-$C_{10}H_{16}$ |
| 15 | Butanesulfonyl(D)Phe-ProboroGly-[(CH$_2$)$_3$—NH-(2-amino-imidazol-5-yl)]-OH |
| 16 | Butanesulfonyl(D)Phe-ProboroGly-[(CH$_2$)$_3$—NH-(2-amino-imidazol-4-yl)]-OH |
| 17 | Hydrocinnamoyl-N-[2-cyclopropylphenethyl]GlyboroGly-[(CH$_2$)$_3$-(2-aminoimidazol-5-yl)-OH |

Utility

The compounds which are described in the present invention represent a novel class of potent, reversible inhibitors of trypsin-like enzymes. Trypsin-like enzymes are a group of proteases which hydrolyzed peptide bonds at basic residues liberating either a C-terminal arginyl or lysyl residue. Among these are enzymes of the blood coagulation and fibrinolytic system required for hemostasis. They are Factors II, X, VII, IX, XII, kallikrein, tissue plasminogen activators, urokinase-like plasminogen activator, and plasmin. Enzymes of the complement system, acrosin (required for fertilization), pancreatic trypsin are also in this group. Elevated levels of proteolysis by these proteases can result in disease states. For example, consumptive coagulopathy, a condition marked by a decrease in the blood levels of enzymes of both the coagulation system, the fibrinolytic system and accompanying protease inhibitors is often fatal. Intervention by a synthetic inhibitor would clearly be valuable. More specifically, proteolysis by thrombin is required for blood clotting. Inhibition of thrombin results in an effective inhibitor of blood clotting. The importance of an effective inhibitor of thrombin is underscored by the observation that conventional anticoagulants such as heparin (and its complex with the protein inhibitor, antithrombin III) are ineffective in blocking arterial thrombosis associated with myocardial infarctions and other clotting disorders. However, a low molecular weight thrombin inhibitor, containing a different functionality, was effective in blocking arterial thrombosis (Hanson and Harker, Proc. Natl. Acad. Sci. U.S.A. 85, 3184 (1988). Therefore, we have chosen to demonstrate utility of compounds in the inhibition of thrombin, both as in buffered solutions and in plasma. Specifically, the compounds have utility as drugs for the treatment of diseases arising from elevated thrombin activity such as myocardial infarction, and as reagents used as anticoagulants in the processing of blood to plasma for diagnostic and other commercial purposes.

Compounds of the present invention are expected to be effective in the control of aberrant proteolysis and a number of accompanying disease states such as inflammation, pancretitis, and heritary angioedema.

Compounds of the present invention were shown to be direct acting inhibitors of the serine protease thrombin by their ability to inhibit the cleavage of small molecule substrates by thrombin in a purified system. The direct interaction of representative examples of the compounds of the present invention with human α-thrombin was demonstrated by x-ray crystallographic analysis of the compounds in complex with human α-thrombin. X-ray diffraction patterns were solved for three dimensional structure and showed that these compounds directly interact with the proteolytic active site of human α-thrombin and that the boronic acid portion of the compounds is in close proximity to the serine which is part of the catalytic triad.

The effectiveness of compounds of the present invention as inhibitors of blood coagulation proteases was determined using purified human proteases and synthetic substrates following procedures similar to those described in Kettner et al. (1990).

For these assays, the rate of enzymatic (thrombin, Factor Xa, and Factor VIIa) hydrolysis of chromogenic substrates (S2238 (H-D-Phe-Pip-Arg-pNA), S2222, and S2288, respectively; Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 run in the presence of inhibitor is indicative of enzyme inhibition. The results of this assay are expressed as inhibitory constant, $K_i$.

Thrombin and Xa determinations were made in 0.10M sodium phosphate buffer, pH 7.5, containing 0.20 M NaCl, and 0.5% PEG 8000. VIIa determinations were made in 0.05M tris buffer, pH 7.6, containing 0.10 M NaCl, 4 mM CaCl$_2$, and 0.1% bovine serum albumin. The Michaelis constant, Km, for substrate hydrolysis was determined at 25° C. using the method of Lineweaver and Burk.

Values of $K_i$ were determined by allowing 0.2–0.5 nM human thrombin or human factor Xa (Enzyme Research Laboratories, South Bend, Ind.), or 50 nM human factor VIIa (BioSpacific, Emeryville, Calif.) react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_o - v_s}{v_s} = \frac{I}{K_i(1 + S/K_m)}$$

where:

$v_o$ is the velocity of the control in the absence of inhibitor;

$v_s$ is the velocity in the presence of inhibitor;

I is the concentration of inhibitor;

$K_i$ is the dissociation constant of the enzyme: inhibitor complex;

S is the concentration of substrate;

$K_m$ is the Michaelis constant.

Using the methodology described above, representative compounds of this invention were evaluated and found to exhibit a $K_i$ of less 20 nM thereby confirming the utility of compounds of the invention as effective inhibitors of human blood coagulation proteases.

These compounds are also useful as anticoagulants for the processing of blood for therapeutic or diagnostic purposes or for the production of blood products or fragments, since contact of blood with the surfaces commonly used for blood collection and storage causes activation of coagulation leading to thrombin formation and clot formation.

Generally, these compounds may be administered orally, parenterally or intravenously to a host to obtain an anti-thrombogenic effect. The dosage of the active compound depends on the mammalian species, body weight, age, and mode of administration as determined by one skilled in the art. In the case of large mammals such as humans, the compounds may be administered alone or in combination with pharmaceutical carriers or diluents at a dose of from 0.02 to 15 mg/kg to obtain the anti-thrombogenic effect, and may be given as a single dose or in divided doses or as a sustained release formulation.

Pharmaceutical carriers or diluents are well known and include sugars, starches and water, which may be used to make tablets, capsules, injectable solutions or the like which can serve as suitable dosage forms for administration of the compounds of this invention. *Remington's Pharmaceutical Sciences*, A. Osol, is a standard reference text which discloses suitable pharmaceutical carriers and dosage forms. The disclosure of this text is hereby incorporated by reference for a more complete teaching of suitable dosage forms for administration of the compounds of this invention.

What is claimed is:

1. A compound of the formula (IA)

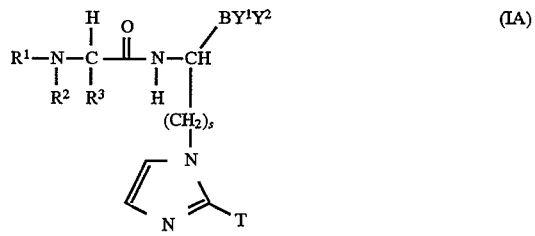

or a pharmaceutically acceptable salt thereof, wherein:

$R^1$ is
  a) $-C(=O)-CH[(CH_2)_nR^4]-NR^5R^6$
  b) $-C(=O)-CR^8R^9-(CH_2)_p-R^4$, or
  c) $-C(=O)-CR^8R^9-W-(CH_2)_r-R^4$;

$R^2$ is
  a) $-CH_2C(R^{12})_2$-aryl, or b)

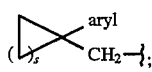

$R^3$ is
  a) hydrogen, or
  b) $R^2$ and $R^3$ can be taken together to form:

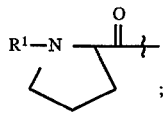

$R^4$ is
  a) aryl, or
  b) $C_3-C_8$ cycloalkyl;

$R^5$ is
  a) hydrogen, or
  b) $-(C_1-C_4 \text{ alkyl})$-aryl;

$R^6$ is
  a) $-C(=O)-R^7$,
  b) $-C(=O)-OR^7$,
  c) $-C(=O)-NR^5R^7$,
  d) $-S(O)_2-R^7$, or
  e) $-S(O)_2-NR_5R^7$;

$R^7$ is
  a) $C_1-C_4$ alkyl, or
  b) $-(C_1-C_4 \text{ alkyl})$-aryl;

$R^8$ and $R^9$ are independently:
  a) hydrogen,
  b) $C_1-C_4$ alkyl,
  d) aryl, or
  e) $-(C_1-C_4 \text{ alkyl})$-aryl;

$R^8$ and $R^9$ can be taken together to form a $(C_3-C_7)$ cycloalkyl;

$R^{12}$ is
  a) $-(C1-C5)\text{alkyl}$, or
  b) $-(C1-C5)\text{fluoroalkyl}$;

aryl as used hereinabove is phenyl or phenyl optionally substituted with from one to three groups selected independently from:

F, Cl, Br, I, $C_1$–$C_4$ alkyl, $C_1$–$C_4$ alkoxy, methylenedioxy, —$NO_2$, —$CF_3$, —$S(O)_r$—($C_1$–$C_4$ alkyl), CN, —OH, —$NH_2$, —NH($C_1$–$C_4$ alkyl), —N($C_1$–$C_4$ alkyl)$_2$, —NHC(=O) ($C_1$–$C_4$ alkyl), —$(CH_2)_p$—$CO_2$($C_1$–$C_4$ alkyl), or phenyl;

T is —$NH_2$;

$Y^1$ and $Y^2$ are
 a) —OH, or
  when taken together $Y^1$ and $Y^2$ form with B:
 b) a cyclic boron ester derived from a diol selected from pinanediol, pinacol, 1,2-ethanediol, 1,3,-propanediol, 1,2-propanediol, 2,3-butanediol, 1,2-diisopropylethanediol, 5,6-decanediol and 1,2-dicyclohexylethanediol;

n is 0 or 1;

p is 0 to 3;

r is 0 to 2;

s is 1 to 4; and t is 1 to 3.

2. A pharmaceutical composition comprising a pharmaceutically suitable carrier and a therapeutically effective amount of a compound of claim 1.

3. A method of treating thrombosis in a mammal by inhibiting trysin-like serine proteases of the coagulation cascade, said method comprising adminstering to an animal in need of such treatment a therapeutically effective amount of a compound of claim 1.

\* \* \* \* \*